US005800849A

United States Patent [19]
Budtz et al.

[11] Patent Number: 5,800,849
[45] Date of Patent: Sep. 1, 1998

[54] CHEESEMAKING WITH RECOMBINANT ASPARTIC PROTEASE

[75] Inventors: Peter Budtz, Frederiksberg; Hans Peter Heldt-Hansen, Virum, both of Denmark

[73] Assignee: Gist-brocades, B.V., Netherlands

[21] Appl. No.: 535,237

[22] PCT Filed: Apr. 22, 1994

[86] PCT No.: PCT/DK94/00163

§ 371 Date: Dec. 29, 1995

§ 102(e) Date: Dec. 29, 1995

[87] PCT Pub. No.: WO94/24880

PCT Pub. Date: Nov. 10, 1994

[30] Foreign Application Priority Data

Apr. 27, 1993 [DK] Denmark ............................ 474/93

[51] Int. Cl.$^6$ ........................................................ A23C 9/12
[52] U.S. Cl. ............................ 426/36; 426/34; 426/38; 426/580; 426/582
[58] Field of Search .................................. 426/34, 36, 37, 426/38, 580, 582, 39, 42, 43, 63

[56] References Cited

U.S. PATENT DOCUMENTS

| | | | |
|---|---|---|---|
| 3,151,039 | 9/1964 | Arima et al. | 426/36 |
| 3,212,905 | 10/1965 | Arima et al. | 426/36 |
| 3,295,991 | 1/1967 | Cort et al. | 426/36 |
| 4,158,607 | 6/1979 | Kalinowski et al. | 426/36 |
| 4,885,249 | 12/1989 | Buxton et al. | |

FOREIGN PATENT DOCUMENTS

| | | |
|---|---|---|
| 0 238 023 | 9/1987 | European Pat. Off. . |
| 0 305 216 | 3/1989 | European Pat. Off. . |
| 0 489 718 | 6/1992 | European Pat. Off. . |

OTHER PUBLICATIONS

Berridge, N.J., "Some Observations on the Determination of the Activity of Rennet," The Analyst, Proceedings of the Society of Public Analysts and Other Analytical Chemists, Meeting, November 7, 1951, vol. 77:57–62.

Buxton, F.P., et al., "Transformation of *Aspergillus niger* using the argB gene of *Aspergillus nidulans*," Gene 37 (1985) 207–214.

Peppler, H.J. and Perlman, D., eds., Microbial Technology, Academic Press, New York, 1979, Second Edition/Vol. I, pp. 294–297.

Quist, K.B., et al., "Fremstilling af Havarti ost ud fra mælk, der er koncentreret ca. 5 gange ved ultrafiltrering" *Beretning fra Statens Mejeriforsog,* 1986.

Saunders, G., et al., "Heterologous gene expression in filamentous fungi," Tibech—Oct. 1989 (vol. 7) pp. 283–287, Elsevier Science Publishers Ltd. (UK).

Yelton, M.M., et al., "Transformation of *Aspergillus nidulans* by using a trpC plasmid," Proc. Natl. Acad. Sci. USA 81:1470–1474 (Mar. 1984).

Primary Examiner—Leslie Wong
Attorney, Agent, or Firm—Morrison & Foerster LLP

[57] ABSTRACT

A process of producing cheese in improved yields, wherein a recombinant aspartic protease, derived from *Rhizomucor miehei* or *Rhizomucor pusillus*, is added to milk in sufficient amounts to effect clotting of the milk, after which the resulting curd is processed in a manner known per se for making cheese.

15 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1416 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 15...1304
        ( D ) OTHER INFORMATION:

( x i ) SEQUENCE DESCRIPTION: SEQ ID NO:1:

```
ATCAGATTCC GACC ATG CTC TTC TCT CAG ATT ACT TCT GCG ATC CTT TTA      50
               Met Leu Phe Ser Gln Ile Thr Ser Ala Ile Leu Leu
                1           5               10
```

| | | | | | | | | | | | | | | | | |
|---|---|---|---|---|---|---|---|---|---|---|---|---|---|---|---|---|
| ACA | GCG | GCT | TCT | TTG | TCG | CTT | ACC | ACT | GCT | CGC | CCG | GTA | TCC | AAG | CAA | 98 |
| Thr | Ala | Ala | Ser | Leu | Ser | Leu | Thr | Thr | Ala | Arg | Pro | Val | Ser | Lys | Gln | |
| | | 15 | | | | 20 | | | | | 25 | | | | | |
| TCC | GAG | TCC | AAG | GAC | AAG | CTT | CTG | GCG | CTT | CCT | CTC | ACC | TCG | GTG | TCC | 146 |
| Ser | Glu | Ser | Lys | Asp | Lys | Leu | Leu | Ala | Leu | Pro | Leu | Thr | Ser | Val | Ser | |
| | 30 | | | | 35 | | | | | 40 | | | | | | |
| CGC | AAG | TTC | TCT | CAA | ACC | AAG | TTC | GGT | CAG | CAA | CAA | CTT | GCT | GAG | AAG | 194 |
| Arg | Lys | Phe | Ser | Gln | Thr | Lys | Phe | Gly | Gln | Gln | Gln | Leu | Ala | Glu | Lys | |
| 45 | | | | | 50 | | | | | 55 | | | | | 60 | |
| CTA | GCA | GGT | CTC | AAG | CCC | TTC | TCT | GAA | GCT | GCC | GCA | GAC | GGC | TCC | GTC | 242 |
| Leu | Ala | Gly | Leu | Lys | Pro | Phe | Ser | Glu | Ala | Ala | Ala | Asp | Gly | Ser | Val | |
| | | | | 65 | | | | | 70 | | | | | 75 | | |
| GAT | ACG | CCC | GGC | TAT | TAC | GAC | TTT | GAT | CTG | GAG | GAG | TAT | GCT | ATT | CCG | 290 |
| Asp | Thr | Pro | Gly | Tyr | Tyr | Asp | Phe | Asp | Leu | Glu | Glu | Tyr | Ala | Ile | Pro | |
| | | | 80 | | | | | 85 | | | | | 90 | | | |
| GTC | TCC | ATT | GGT | ACT | CCT | GGT | CAA | GAC | TTT | TTG | CTC | TTG | TTC | GAC | ACT | 338 |
| Val | Ser | Ile | Gly | Thr | Pro | Gly | Gln | Asp | Phe | Leu | Leu | Leu | Phe | Asp | Thr | |
| | | 95 | | | | | 100 | | | | | 105 | | | | |
| GGC | AGC | TCC | GAT | ACT | TGG | GTT | CCA | CAC | AAG | GGT | TGC | ACC | AAG | TCT | GAA | 386 |
| Gly | Ser | Ser | Asp | Thr | Trp | Val | Pro | His | Lys | Gly | Cys | Thr | Lys | Ser | Glu | |
| | 110 | | | | | 115 | | | | | 120 | | | | | |
| GGT | TGT | GTT | GGC | AGC | CGA | TTC | TTT | GAT | CCA | TCG | GCT | TCC | TCC | ACT | TTT | 434 |
| Gly | Cys | Val | Gly | Ser | Arg | Phe | Phe | Asp | Pro | Ser | Ala | Ser | Ser | Thr | Phe | |
| 125 | | | | | 130 | | | | | 135 | | | | | 140 | |
| AAA | GCA | ACT | AAC | TAC | AAC | CTA | AAC | ATC | ACC | TAC | GGT | ACT | GGC | GGC | GCA | 482 |
| Lys | Ala | Thr | Asn | Tyr | Asn | Leu | Asn | Ile | Thr | Tyr | Gly | Thr | Gly | Gly | Ala | |
| | | | | 145 | | | | | 150 | | | | | 155 | | |
| AAC | GGT | CTT | TAC | TTT | GAA | GAC | AGC | ATC | GCT | ATC | GGC | GAC | ATC | ACC | GTG | 530 |
| Asn | Gly | Leu | Tyr | Phe | Glu | Asp | Ser | Ile | Ala | Ile | Gly | Asp | Ile | Thr | Val | |
| | | | 160 | | | | | 165 | | | | | 170 | | | |
| ACC | AAG | CAA | ATT | CTG | GCT | TAC | GTC | GAT | AAT | GTT | CGC | GGC | CCA | ACT | GCT | 578 |
| Thr | Lys | Gln | Ile | Leu | Ala | Tyr | Val | Asp | Asn | Val | Arg | Gly | Pro | Thr | Ala | |
| | | 175 | | | | | 180 | | | | | 185 | | | | |
| GAG | CAG | TCT | CCT | AAC | GCT | GAC | ATT | TTC | CTT | GAT | GGT | CTC | TTT | GGT | GCA | 626 |
| Glu | Gln | Ser | Pro | Asn | Ala | Asp | Ile | Phe | Leu | Asp | Gly | Leu | Phe | Gly | Ala | |
| | 190 | | | | | 195 | | | | | 200 | | | | | |
| GCC | TAC | CCA | GAC | AAC | ACG | GCC | ATG | GAA | GCA | GAG | TAT | GGA | TCG | ACT | TAT | 674 |
| Ala | Tyr | Pro | Asp | Asn | Thr | Ala | Met | Glu | Ala | Glu | Tyr | Gly | Ser | Thr | Tyr | |
| 205 | | | | | 210 | | | | | 215 | | | | | 220 | |
| AAC | ACT | GTT | CAC | GTC | AAC | CTC | TAC | AAG | CAA | GGC | TTG | ATC | TCT | TCT | CCT | 722 |
| Asn | Thr | Val | His | Val | Asn | Leu | Tyr | Lys | Gln | Gly | Leu | Ile | Ser | Ser | Pro | |
| | | | | 225 | | | | | 230 | | | | | 235 | | |
| CTT | TTC | TCG | GTC | TAC | ATG | AAC | ACT | AAC | AGC | GGC | ACT | GGA | GAG | GTC | GTC | 770 |
| Leu | Phe | Ser | Val | Tyr | Met | Asn | Thr | Asn | Ser | Gly | Thr | Gly | Glu | Val | Val | |
| | | | 240 | | | | | 245 | | | | | 250 | | | |
| TTT | GGT | GGA | GTC | AAC | AAC | ACG | CTT | CTC | GGC | GGC | GAC | ATT | GCC | TAC | ACG | 818 |
| Phe | Gly | Gly | Val | Asn | Asn | Thr | Leu | Leu | Gly | Gly | Asp | Ile | Ala | Tyr | Thr | |
| | | 255 | | | | | 260 | | | | | 265 | | | | |
| GAC | GTT | ATG | AGT | CGT | TAT | GGT | GGT | TAT | TAC | TTC | TGG | GAC | GCA | CCC | GTC | 866 |
| Asp | Val | Met | Ser | Arg | Tyr | Gly | Gly | Tyr | Tyr | Phe | Trp | Asp | Ala | Pro | Val | |
| | 270 | | | | 275 | | | | | 280 | | | | | | |
| ACA | GGT | ATC | ACC | GTC | GAT | GGA | TCT | GCT | GCT | GTC | AGG | TTC | TCG | AGA | CCC | 914 |
| Thr | Gly | Ile | Thr | Val | Asp | Gly | Ser | Ala | Ala | Val | Arg | Phe | Ser | Arg | Pro | |
| 285 | | | | | 290 | | | | | 295 | | | | | 300 | |
| CAA | GCA | TTC | ACC | ATC | GAT | ACT | GGC | ACC | AAC | TTT | TTC | ATT | ATG | CCC | TCA | 962 |
| Gln | Ala | Phe | Thr | Ile | Asp | Thr | Gly | Thr | Asn | Phe | Phe | Ile | Met | Pro | Ser | |
| | | | | 305 | | | | | 310 | | | | | 315 | | |
| AGC | GCC | GCT | TCT | AAG | ATT | GTC | AAA | GCA | GCT | CTC | CCT | GAT | GCC | ACT | GAA | 1010 |
| Ser | Ala | Ala | Ser | Lys | Ile | Val | Lys | Ala | Ala | Leu | Pro | Asp | Ala | Thr | Glu | |
| | | | 320 | | | | | 325 | | | | | 330 | | | |

-continued

| | | | | | | | | | | | | | | | | |
|---|---|---|---|---|---|---|---|---|---|---|---|---|---|---|---|---|
| ACC | CAG | CAG | GGC | TGG | GTT | GTT | CCT | TGC | GCT | AGC | TAC | CAG | AAC | TCC | AAG | 1058 |
| Thr | Gln | Gln | Gly | Trp | Val | Val | Pro | Cys | Ala | Ser | Tyr | Gln | Asn | Ser | Lys | |
| | | 335 | | | | 340 | | | | | 345 | | | | | |
| TCG | ACT | ATC | AGC | ATC | GTC | ATG | CAA | AAG | TCC | GGC | TCA | AGC | AGT | GAC | ACT | 1106 |
| Ser | Thr | Ile | Ser | Ile | Val | Met | Gln | Lys | Ser | Gly | Ser | Ser | Ser | Asp | Thr | |
| | 350 | | | | | 355 | | | | | 360 | | | | | |
| ATT | GAG | ATC | TCG | GTT | CCT | GTC | AGC | AAA | ATG | CTT | CTT | CCA | GTC | GAC | CAA | 1154 |
| Ile | Glu | Ile | Ser | Val | Pro | Val | Ser | Lys | Met | Leu | Leu | Pro | Val | Asp | Gln | |
| 365 | | | | | 370 | | | | | 375 | | | | | 380 | |
| TCG | AAC | GAG | ACT | TGC | ATG | TTT | ATC | ATT | CTT | CCC | GAC | GGT | GGT | AAC | CAG | 1202 |
| Ser | Asn | Glu | Thr | Cys | Met | Phe | Ile | Ile | Leu | Pro | Asp | Gly | Gly | Asn | Gln | |
| | | | | 385 | | | | | 390 | | | | | 395 | | |
| TAC | ATT | GTT | GGC | AAC | TTG | TTC | CTG | CGC | TTC | TTT | GTC | AAT | GTT | TAC | GAC | 1250 |
| Tyr | Ile | Val | Gly | Asn | Leu | Phe | Leu | Arg | Phe | Phe | Val | Asn | Val | Tyr | Asp | |
| | | | 400 | | | | | 405 | | | | | 410 | | | |
| TTT | GGC | AAC | AAC | CGT | ATC | GGC | TTT | GCA | CCT | TTG | GCC | TCG | GCT | TAT | GAA | 1298 |
| Phe | Gly | Asn | Asn | Arg | Ile | Gly | Phe | Ala | Pro | Leu | Ala | Ser | Ala | Tyr | Glu | |
| | | 415 | | | | | 420 | | | | | 425 | | | | |
| AAC | GAG | TAAAGGGGCA | CCAATTCTTC | TTTAGCTGCT | CAGATAACTT | TGTAACTCTC | TG | | | | | | | | | 1356 |
| Asn | Glu | | | | | | | | | | | | | | | |
| | 430 | | | | | | | | | | | | | | | |

ATATACTCTT TATAACCTTT ATTTCTCACT TTTTAACTGT ATTCCAATAC ATTATTTCCT 1416

1416

( 2 ) INFORMATION FOR SEQ ID NO:2:

( i ) SEQUENCE CHARACTERISTICS:
    ( A ) LENGTH: 430 amino acids
    ( B ) TYPE: amino acid
    ( C ) STRANDEDNESS: single
    ( D ) TOPOLOGY: linear ( i i ) MOLECULE TYPE: protein ( v ) FRAGMENT TYPE: internal ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Leu | Phe | Ser | Gln | Ile | Thr | Ser | Ala | Ile | Leu | Leu | Thr | Ala | Ala | Ser |
| 1 | | | | 5 | | | | | 10 | | | | | 15 | |
| Leu | Ser | Leu | Thr | Thr | Ala | Arg | Pro | Val | Ser | Lys | Gln | Ser | Glu | Ser | Lys |
| | | | 20 | | | | | 25 | | | | | 30 | | |
| Asp | Lys | Leu | Leu | Ala | Leu | Pro | Leu | Thr | Ser | Val | Ser | Arg | Lys | Phe | Ser |
| | | 35 | | | | | 40 | | | | | 45 | | | |
| Gln | Thr | Lys | Phe | Gly | Gln | Gln | Gln | Leu | Ala | Glu | Lys | Leu | Ala | Gly | Leu |
| | 50 | | | | | 55 | | | | | 60 | | | | |
| Lys | Pro | Phe | Ser | Glu | Ala | Ala | Ala | Asp | Gly | Ser | Val | Asp | Thr | Pro | Gly |
| 65 | | | | | 70 | | | | | 75 | | | | | 80 |
| Tyr | Tyr | Asp | Phe | Asp | Leu | Glu | Glu | Tyr | Ala | Ile | Pro | Val | Ser | Ile | Gly |
| | | | | 85 | | | | | 90 | | | | | 95 | |
| Thr | Pro | Gly | Gln | Asp | Phe | Leu | Leu | Leu | Phe | Asp | Thr | Gly | Ser | Ser | Asp |
| | | | 100 | | | | | 105 | | | | | 110 | | |
| Thr | Trp | Val | Pro | His | Lys | Gly | Cys | Thr | Lys | Ser | Glu | Gly | Cys | Val | Gly |
| | | | 115 | | | | 120 | | | | | 125 | | | |
| Ser | Arg | Phe | Phe | Asp | Pro | Ser | Ala | Ser | Ser | Thr | Phe | Lys | Ala | Thr | Asn |
| | | 130 | | | | | 135 | | | | | 140 | | | |
| Tyr | Asn | Leu | Asn | Ile | Thr | Tyr | Gly | Thr | Gly | Gly | Ala | Asn | Gly | Leu | Tyr |
| 145 | | | | | 150 | | | | | 155 | | | | | 160 |
| Phe | Glu | Asp | Ser | Ile | Ala | Ile | Gly | Asp | Ile | Thr | Val | Thr | Lys | Gln | Ile |
| | | | | 165 | | | | | 170 | | | | | 175 | |

```
Leu Ala Tyr Val Asp Asn Val Arg Gly Pro Thr Ala Glu Gln Ser Pro
            180                 185                 190
Asn Ala Asp Ile Phe Leu Asp Gly Leu Phe Gly Ala Ala Tyr Pro Asp
        195                 200                 205
Asn Thr Ala Met Glu Ala Glu Tyr Gly Ser Thr Tyr Asn Thr Val His
    210                 215             220
Val Asn Leu Tyr Lys Gln Gly Leu Ile Ser Ser Pro Leu Phe Ser Val
225                 230             235                         240
Tyr Met Asn Thr Asn Ser Gly Thr Gly Glu Val Val Phe Gly Gly Val
                245                 250                 255
Asn Asn Thr Leu Leu Gly Gly Asp Ile Ala Tyr Thr Asp Val Met Ser
            260                 265                 270
Arg Tyr Gly Gly Tyr Tyr Phe Trp Asp Ala Pro Val Thr Gly Ile Thr
        275                 280                 285
Val Asp Gly Ser Ala Ala Val Arg Phe Ser Arg Pro Gln Ala Phe Thr
    290                 295                 300
Ile Asp Thr Gly Thr Asn Phe Phe Ile Met Pro Ser Ser Ala Ala Ser
305                 310                 315                     320
Lys Ile Val Lys Ala Ala Leu Pro Asp Ala Thr Glu Thr Gln Gln Gly
            325                 330                 335
Trp Val Val Pro Cys Ala Ser Tyr Gln Asn Ser Lys Ser Thr Ile Ser
            340                 345                 350
Ile Val Met Gln Lys Ser Gly Ser Ser Ser Asp Thr Ile Glu Ile Ser
        355                 360                 365
Val Pro Val Ser Lys Met Leu Leu Pro Val Asp Gln Ser Asn Gln Thr
    370                 375                 380
Cys Met Phe Ile Ile Leu Pro Asp Gly Gly Asn Gln Tyr Ile Val Gly
385                 390                 395                     400
Asn Leu Phe Leu Arg Phe Phe Val Asn Val Tyr Asp Phe Gly Asn Asn
            405                 410                 415
Arg Ile Gly Phe Ala Pro Leu Ala Ser Ala Tyr Glu Asn Glu
            420                 425                 430
```

CHEESEMAKING WITH RECOMBINANT ASPARTIC PROTEASE

This is a National stage filing of PCT/DK94/00163 filed Apr. 22, 1994.

FIELD OF INVENTION

This invention relates to a process for producing cheese in improved yields.

BACKGROUND OF THE INVENTION

In the production of cheese it is necessary to coagulate the milk in order to be able to separate the casein from the whey. Products containing rennin, which is a milk coagulating enzyme isolated from calf stomachs, have for many years been used for this purpose. Shortage of calf stomachs has in the last decades resulted in intense searches for other milk coagulating enzymes. Today, bovine pepsin, porcine pepsin, as well as microbial enzymes are being used commercially. The most useful among the microbial rennets are *Rhizomucor miehei* rennet and *Rhizomucor pusillus* rennet.

SUMMARY OF THE INVENTION

In this invention it is surprisingly found that the glycosylation of the aspartic protease can give an increase in cheese yield of 0.2% compared with the native enzyme. An increase in cheese yield of 0.2% would mean an extra 2 kg of cheese per one ton of cheese having a value of about 8–10 US$ (prices of the dairy).

Accordingly, the present invention relates to a process of producing cheese in improved yields, wherein a recombinant aspartic protease is added to milk in sufficient amounts to effect clotting of the milk, after which the resulting curd is processed in a manner known per se for making cheese.

The term "recombinant aspartic protease" is applied to (pro) chymosin or microbial aspartic protease produced in a host organism transformed with DNA coding for the protease. The host organism may conveniently be a fungus, e.g. a yeast or a filamentous fungus.

The term "filamentous fungus" is intended to include fungi belonging to the groups Phycomycetes, Zygomycetes, Ascomycetes, Basidiomycetes or fungi imperfecti, including Hyphomycetes such as the genera Asperaillus, Trichoderma, Penicillium, Fusarium or Humicola.

DETAILED DISCLOSURE OF THE INVENTION
Protease

According to this invention it is preferred to use recombinant aspartic protease from Mucorales (e.g. Rhizomucor, in particular *Rhizomucor miehei* or *Rhizomucor pusillus*) expressed in Aspergillus or Trichoderma in a process of producing cheese in improved yields.

A DNA sequence encoding bovine prochymosin or preprochymosin may for instance be obtained as described in EP 215 594. A DNA sequence encoding *Rhizomucor miehei* aspartic protease may be isolated as described in EP 238 023. The nucleotide sequence encoding *Rhizomucor miehei* aspartic protease is set forth herein as SEQ ID NO: 2. The nucleotide sequence encoding *Rhizomucor miehei* aspartic protease is set forth herein as SEQ ID NO: 1. The deduced amino acid sequence is set forth as SEQ ID NO:2.

DNA sequences encoding functions facilitating gene expression typically comprise a promoter, transcription initiation sites, and transcription termination and polyadenylation functions.

The promoter which may be preceded by upstream activating sequences and enhancer sequences as known in the art may be any DNA sequence exhibiting a strong transcriptional activity in filamentous fungi and may be derived from a gene encoding an extracellular or intracellular protein such as an amylase, a glucoamylase, a protease, a lipase or a cellulase.

Examples of suitable promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease or *A. oryzae* triose phosphate isomerase.

The filamentous fungus host organism may conveniently be one which has previously been used as a host for producing recombinant proteins, e.g. a strain of *Asperaillus sp.*, such as *A. niger, A. nidulans* or *A. oryzae*. The use of *A. oryzae* in the production of recombinant proteins is extensively described in e.g. EP 238 023.

Termination and polyadenylation sequences may suitably be derived from the same sources as the promoter.

The techniques used to transform a fungal host cell may suitably be adapted from the methods of transforming *A. nidulans* described in, for instance, Yelton et al., *Proc. Natl. Acad. Sci. USA* 81, 1984, pp. 1470–1474, or EP 215 594, or from the methods of transforming *A. niger* described in, for instance Buxton et al., *Gene* 37, 1985, pp 207–215 or U.S. Pat. No. 4,885,249, or from the method of transforming *A. oryzae* described in EP 238023. In the process of the present invention, the host cell is transformed with a vector system comprising a DNA sequence coding for a selection marker which is capable of being incorporated in the genome of the host organism on transformation, but which is either not expressed by the host before transformation or expressed in amounts which are not sufficient to permit growth under selective conditions. Transformants can then be selected and isolated from non-transformants on the basis of the incorporated selection marker.

Suitable selection markers are derived from the *A. nidulans* or *A. niger argB* gene, the *A. nidulans trpC* gene, the *A. nidulans amdS* gene, the *Neurospora crassa pyr4* or *DHFR* genes, or the *A. niger* or *A. oryzae niaD* gene.

The DNA sequences coding for the aspartic protease, promoter and terminator may be inserted in a vector containing the selection marker, or it may be inserted in a separate vector for introduction into the host cell. In the present context, the term "vector system" is intended to include a single vector or two or more vectors which together contain the total DNA information to be introduced into the host cell. The vector or vectors may be linear or closed circular molecules. In a preferred embodiment of the process of the invention, the vector system comprises two vectors, one carrying the DNA sequence coding for the selection marker, and the other carrying the DNA sequences encoding the heme protein, the preregion and the functions facilitating gene expression.

The extent of glycosylation of the recombinant aspartic protease has surprisingly been found to be higher than the glycosylation of the aspartic proteases obtained from naturally occurring Rhizomucor strains. More specifically ,the novel recombinant aspartic protease is characterized in that the carbohydrate content is of at least 50% more than the native aspartic protease, preferably the carbohydrate content is of a level of 100% more than the native aspartic protease. The term "native aspartic protease" is intended to indicate the protease produced by an organism in nature (e.g. in calf stomach or by a microorganism such as Rhizomucor).

Differentiation and identification of the native aspartic protease and of the recombinant aspartic protease is possible through measurement of their glycosylation.

It has formerly been described that Aspercillus glycosylates Humicola lipase in a different way from the native Humicola lipase (see EP 305 216), but it is new that Aspergillus also glycosylates Rhizomucor aspartic protease differently from the native Rhizomucor aspartic protease, and specifically that by this process the carbohydrate content of the aspartic protease increases by 50–100%.

Analysis of the Amount of N-bound Glycosylation

The amount of N-bound glycosylation is determined as the difference in molecular weights between the aspartic protease and a deglycosylated aspartic protease. The deglycosylation is performed by Endoglycosidase H (from Genzyme) (removes N-bound glycosylation) using 1 mg/ml protease and a reaction time of 18 hour at 37° C., the Endo H is dosed so that no additional deglycosylation is obtained at increased Endo H dosages. The MW weight is measured by SDS-PAGE.

The amount of N-bound glycosylation is expressed in kD glycosylation per mole protein.

Cheesemaking

Any type of milk, in particular milk from ruminants such as cows, sheep, goats or camels, may be used as the starting material in the process of the invention, e.g. as reconstituted milk, whole milk, concentrated whole milk or skimmilk.

The milk may be concentrated in various ways such as by evaporation or spray-drying, but is preferably concentrated by membrane filtration, i.e. ultrafiltration in which molecules with a molecular weight of up to 20,000 are allowed to pass the membrane, optionally with diafiltration before or after ultrafiltration, or possibly hyperfiltration in which molecules of a molecular weight of up to 500 are allowed to pass the membrane. For a more detailed description of the ultrafiltration process, see for instance Quist et al., *Beretning fra Statens Mejeriforsøg*, 1986.

A starter culture may be added to the milk before or simultaneously with the addition of the recombinant aspartic acid in the present invention. The starter culture is a culture of lactic acid bacteria used, in conventional cheesemaking, to ferment the lactose present in the milk and to cause further decomposition of the clotted casein into smaller peptides and free amino acids as a result of their production of proteases and peptidases. The starter culture may be added in amounts which are conventional for the present purpose, i.e. typically amounts of about $1 \times 10^4$–$1 \times 10^5$ bacteria/g of cheese milk, and may be added in the form of freeze-dried, frozen or liquid cultures. When the milk employed in the process of the invention is concentrated milk, it is preferred to add the starter culture after concentrating the milk, although this is not an absolute requirement, as the starter bacteria will be retained during filtration.

After adding the milk clotting enzyme the subsequent steps in the cheesemaking process, i.e. further salting, pressing, and ripening the curd, may be conducted in the traditional way of producing cheese, e.g. as described by R. Scott, *Cheesemaking in Practice*, 2nd Ed., Elsevier, London, 1986.

It is at present contemplated that most types of cheese may advantageously be prepared by the process of the invention.

The present invention relates to an aspartic protease preparation in liquid, stabilized, spray-dried, vacuum-dried, freeze-dried or granulated form, or immobilized on a suitable carrier.

The various ways in which the enzyme preparation may be formulated are well known in the enzyme art, cf. for instance K. Aunstrup et al., "Production of Microbial Enzymes", in *Microbial Technology* (H. J. Peppler and D. Perlman, Eds.), 2nd Ed., Vol I, Academic Press 1979, pp 295–297.

In the process of the present invention the amount of recombinant aspartic protease will vary according to the degree of concentration of the milk, but the enzyme will usually be added in an amount of 1–10 KRU per 1 l of whole milk.

Rennet Strength

1 RU is the Novo unit of rennet strength. 1 KRU=1000 RU. The rennet strength is determined by using a modified Berridge method (N. J. Berridge, *Analyst*, 77, 1952, p. 57) where the rennet strength is determined by using a Rennilase® (*Rhizomucor miehei* aspartic protease available from Novo Nordisk A/S) powder standard as a reference.

The principle of the method is that the enzyme acts upon a solution of skimmed milk powder containing calcium chloride under standard conditions. The time needed from the addition of the enzyme until the reaction mixture begins to show flocculation is measured. This time is approximately inversely proportional with the enzyme concentration and is compared with the flocculation time for a sample with known enzyme strength. These times should not differ substantially from each other, and they should amount to 5.0 min±0.5 min.

The determination of strength is carried out visually and is performed at 30° C. "Berridge Substrate" consisting of 12 g of spray-dried skimmed milk powder dissolved in 100 ml of 0.01M calcium chloride solution is used. The substrate must stand for at least 1 hour before it can be used.

The analysis is performed in a glass water bath in which the test tubes by means of a motor are slowly rotated about their longitudinal axes with an inclination of about 30° relative to the water surface. A film of milk will thereby continuously be formed on the tube above the milk surface, and it is easy to see the flocculation in this film as soon as it starts.

Sometimes local clottings can take place in the milk. These clottings are not to be confused with the actual floculation which is characterized by the adhesion of small flakes of casein to the test tube near the milk surface.

About half an hour before the analysis is carried out place stoppered test tubes containing 10 ml of milk substrate in the constant temperature water bath at 30° C.±0.1° C. The flocculation time changes slightly with the time in which the substrate is kept warm. Now add with a syringe one ml of the diluted enzyme solution to each of the 3 test tubes and simultaneously activate a stop watch for each tube. The stop watch is started immediately after the enzyme solution has been injected into the test tube. The enzyme solution is injected against the wall of the tube to avoid foaming of the milk. Immediately after the addition of the enzyme, the test tube is closed with a clean, dry stopper and inverted 3 times so as to wash all the enzyme off the tube wall and into the milk. The first test tube may immediately thereafter be placed on the rotating spindle. At the point in time when small flakes of coagulum start being deposited on the tube the stop watch for the first tube is stopped, the tube is replaced with tube No. 2 etc. Try to achieve a flocculation time between 4.5 and 5.5 min. The flocculation time for the 3 test tubes must not vary more than 0.1 min (6 sec.), and the average is used to calculate the strength of the rennet.

Calculation of the Rennet Strength

Strength of sample =

$$\frac{\text{Strength of standard} \times \text{Flocculation time of dilut. of stand.}}{\text{Flocculation time of sample}} \times \frac{\text{Dilution of sample}}{\text{Dilution of standard}}$$

The modified Berridge method is only suited for the determination of rennet strengths of rennets without added calcium salts.

The invention is further illustrated in the following examples which are not intended to be in any way limiting to the scope of the invention as claimed.

EXAMPLE 1

Cheese Yield Using *Aspergillus oryzae* produced Aspartic Protease and Rennilase® XL Enzymes

*Aspergillus oryzae* produced protease: Transformant p777 (described in EP 489 718) was fermented for approx. 5 days in a conventional agitated and aerated 2.5 m³ fermentor on a medium containing soya grits supplied with maltodextrin during growth, the pH was kept below 6.0 by addition of phosphoric acid. EP 489,718 is a divisional of EP 238,023 referenced above, and the nucleotide sequence encoding the aspartic protease is as described therein—i.e., in SEQ ID NO:1 and SEQ ID NO:2. The aspartic protease was recovered from the fermentation broth by conventional filtration, ultrafiltration, and evaporation techniques. The aspartic protease was destabilized as described in U.S. Pat. No. 4,357,357. The aspartic protease concentrate was diluted to 54.63 KRU/g.

*Rhizomucor miehei* produced aspartic protease: Rennilase® XL 51.42 KRU/g was used (available from Novo Nordisk A/S).

Both enzymes were used so that the first sign of flocculation appeared after about 15 min. Dosages were kept at constant level throughout the experiment. Variations in the coagulability of the milk was compensated by varying cutting times.

Cheesemaking in Beakers

To a 5 l beaker 4000 g of whole pasteurized milk (available from MD Foods, Karolinevej 1, DK-4200 Slagelse, Denmark) was added.

A starter culture CHL 113 batch 010691 (available from Chr. Hansen, Bøge Alle 10, DK-2970 Hørsholm, Denmark) was incubated for 16 hours in sufficient amount of milk at room temperature and frozen in 40 g portions, enough portions for the entire experiment.

$CaCl_2$ 0.8 g per portion and a thawed portion of starter culture are added. After 30 min ripening time the milk coagulating enzyme in an amount of 10.9 KRU per 4000 g of milk was introduced. Both enzymes were used in each trial, and their order was not randomized. Flocculation time was around 15 min, and the cutting time was approx. 2 times flocculation time plus 1 min. After a healing time of 4 min and a stirring time of 15 min the curd and whey were transferred to a mould with cheese-cloth and left to drain overnight.

Analysis

Well mixed total whey was filtered through one layer of gauze to remove curd particles. Total N was determined using a modified Kjeldal method on a Tecator Digestor and Kjeltec 1003 Distilling System. Protein was expressed as N×6.38. All analysis were done in triplicate.

A paired t test was used on n=61 differences in total protein content of whey, using $t = x_{mean}/(s^2/n)^{1/2}$ as an estimate, where X is the difference in total whey protein between the corresponding experiments with the two enzymes, and $S^2$ is the estimated variation of X, $t_{0.95}(60\%) = 1.67$, $t_{0.995}(60\%) = 3.23$.

Results

In Table 1 some parameters of manufacture of Feta Cheese can be found. Coagulation times averaged 15.41 min for aspartic protease and 15.35 min for Rennilase XL. δprotein was calculated as the difference between the amount of Rennilase XL Whey times protein % deducting the amount of Aspartic Protease Whey times protein %. Average protein loss was found to be 30.30 g with aspartic protease whey and 30.50 g with Rennilase XL whey. These figures could mean an increase in cheese yield of 0.2%, when changing from Rennilase XL to aspartic protease.

$X_{mean}$ on δprotein was found to be −0.1953 and s to be 0.4642 and n=61, and thus an estimate for t can be calculated as $t_e = -0.1953/(0.4642^2/61)^{1/2} = -3.2860$, which means that the hypothesis that no difference between yields can be rejected with very high probability (p<0.001).

TABLE 1

| Some parameters of manufacture of Feta Cheese | | | |
|---|---|---|---|
| parameter | mean | n | s |
| Milk, amount | 4000 g | | constant |
| Starter | 1% | | constant |
| Milk coagulating enzyme KRU/4000 g | | | |
| Aspartic protease | 10.9 | 61 | constant |
| Rennilase ® XL | 10.9 | 61 | constant |
| $CaCl_2$ | 0.02% | | constant |
| Times min | | | |
| ripening flocculation | 30 | 122 | constant |
| Aspartic protease | 15.41 | 61 | ±0.63 |
| Rennilase XL | 15.35 | 60 | ±0.64 |
| cutting time | | | |
| Aspartic protease | 31.79 | 61 | ±1.25 |
| Rennilase XL | 31.82 | 60 | ±1.21 |
| healing time | 4 | | constant |
| stirring | 15 | | constant |
| scooping | 10 | | constant |
| scooping to press | 120 | | constant |
| pH | | | |
| milk | 6.69 | 122 | — |
| setting | 6.57 | 122 | ±0.05 |
| whey | | | |
| Aspartic protease | 6.53 | 56 | ±0.14 |
| Rennilase XL | 6.53 | 51 | 0.14 |
| Temperatures °C. | | | |
| setting | 33 | | |
| Weights g | | | |
| milk | 4000 | 122 | constant |
| whey | 3299.3 | 122 | ±27.5 |
| curd | 685.7 | 117 | ±20.6 |
| Recovery % | | | |
| outputs/inputs | 99.9 | | |
| whey/outputs | 82.8 | | |
| curd/outputs | 17.2 | | |

EXAMPLE 2

Deglycosylation by EndoH of Aspartic Protease Expressed from *Rhizomucor miehei* and *Aspergillus oryzae*

Aspartic protease is a glycosylated protein both when expressed from *R. miehei* and from *A. oryzae*. Endoglycosidase H can liberate the glyco part from N-glycosylated proteins by specific hydrolysis between two N-acetylglucosamine molecules which are bound to Asn in N-glycosylated proteins.

Samples

The *Aspergillus oryzae* produced aspartic protease (produced as described in Example 1) was purified from the culture broth by the method described in Journal of Chromatography 476 (1989) 227–233.

The *Rhizomucor miehei* produced aspartic protease was purified from Rennilase 1500® L (available from Novo Nordisk A/S) by the method described in Journal of Chromatography 476: (1989) 227–233.

Experimental:

*Aspergillus oryzae* produced aspartic protease and *Rhizomucor miehei* produced aspartic protease were incubated at a concentration of 1 mg/ml with EndoH (genzyme) for 18 hours at 37° C. in 100 mM phosphate buffer at pH 6.0. The degree of hydrolysis was determined from the change in MW by SDS-PAGE in 5–20% gradient gels.

Results:

The experiment showed that 0.02 U/ml EndoH was sufficient for almost total deglycosylation, and that the MW of the aspartic protease molecule did not change when incubated without EndoH.

The MW of the deglycosylated aspartic protease was 38.3 kD both from *R. miehei* and *A. oryzae*, whereas the glycosylated enzyme from *R. miehei* showed a MW of 41.5 kD, and the glycosylated enzyme from *A. oryzae* showed a MW of 44.7 kD.

The N-bound glycosylation content of the *A. oryzae* expressed aspartic protease is then 6.4 kD (44.7 kD minus 38.3 kd) per mole protein, being 100% more than the 3.2 kD (41.5 kD –38.3 kD) N-bound glycosylation per mole Rennilase (*R. miehei* expressed aspartic protease).

EXAMPLE 3

Glycolysation of Aspartic Protease

Samples The *Aspergillus oryzae* produced aspartic protease (produced as described in Example 1) was purified from the culture broth by the method described in Journal of Chromatography 476 (1989) 227–233.

The *Rhizomucor miehei* produced aspartic protease was purified from Rennilase 1500® L (available from Novo Nordisk A/S) by the method described in Journal of Chromatography 476: (1989) 227–233.

Both the purified enzymes were freeze dried.

Determination of the Glycosylation

25 μg samples were hydrolysed in 2M TFA (trifluoroacetic acid) in a micro-oven.

The monosaccharides were separated and detected by a Dionex high performance anionic exchange chromatography (HPAEC), the separations were performed by an isocratic elution in 16 mM NaOH. The monosaccharides were detected by pulsed amperometric detection (ref: Rocklin and Pohl;, J. Liq. Chromatography 6: 1577–1590).

The analysed samples are equivalent to 20 μg dry-matter (sample).

The samples were analysed in triplicate.

Results

|  | *Rhizomucor miehei* produced aspartic protease | *Aspergillus oryzae* produced aspartic protease |
| --- | --- | --- |
| Galactosamin | 0 | 0 |
| Glucoseamin | 265 | 630 |
| Galactose | 170 | 500 |
| Glucose | 200 | 100 |
| Mannose | 1300 | 2860 |

The results are given in relative amounts.

It is observed that there are significant differences in the sugar content between the *A. oryzae* expressed aspartic protease and the *R. miehei* expressed aspartic protease, and that the recombinant aspartic protease has an N-bound glucoseamin, galactose and mannose content of 100% more than the native protease.

---

We claim:

1. An improved method for producing cheese using aspartic protease to coagulate milk, wherein said improvement comprises the step of adding a recombinant aspartic protease to milk in sufficient amounts to effect clotting of the milk, wherein said recombinant aspartic protease is produced using a DNA molecule encoding an aspartic protease isolated from a filamentous fungus of the genus Rhizomucor and is expressed in a host selected from the group consisting of the genus Aspergillus and Trichoderma and said recombinant aspartic protease has more N-bound carbohydrates than found in the aspartic protease produced by the fungal source of the DNA molecule encoding said aspartic protease.

2. The method according to claim 1, wherein said DNA molecule encoding said recombinant aspartic protease is isolated from a fungus selected from the group consisting of *Rhizomucor miehei* and *Rhizomucor pusillus*.

3. The method according to claim 1, wherein-said recombinant aspartic protease is expressed in a host selected from the group consisting of *Aspergillus oryzae, A. niger, A. nidulans, A awamori* and *Trichoderma reesei*.

4. The method according to claim 1, wherein said recombinant aspartic protease is added in an amount of 1–10 KRU per liter of milk.

5. The method according to claim 1, wherein the milk is whole milk or concentrated milk.

6. The method according to claim 1, wherein a starter culture is added to the milk before or simultaneously with the addition of said recombinant aspartic protease.

7. The method of claim 1, wherein said recombinant aspartic protease has 50% more, or greater, N-bound carbohydrates than found in the aspartic protease produced by the fungal source of the DNA molecule encoding said aspartic protease.

8. An improved method for producing cheese using aspartic protease to coagulate milk, wherein said improvement comprises the step of adding a recombinant aspartic protease to milk in sufficient amounts to effect clotting of the milk, wherein said recombinant aspartic protease has more N-bound carbohydrates than found in the aspartic protease produced by the fungal source of the DNA molecule encoding said aspartic protease.

9. The method according to claim 8, wherein the recombinant aspartic protease is encoded by a DNA molecule isolated from a filamentous fungus.

10. The method according to claim 9, wherein said DNA molecule encoding said recombinant aspartic protease is isolated from a fungus selected from the group consisting of *Rhizomucor miehei* and *Rhizomucor pusillus*.

11. The method according to claim 8, wherein said recombinant aspartic protease is expressed in a host selected from the group consisting of *Aspergillus oryzae, A. niger, A. nidulans, A awamori* and *Trichoderma reesei*.

12. The method according to claim 8, wherein said recombinant aspartic protease is added in an amount of 1–10 KRU per liter of milk.

13. The method according to claim 8, wherein the milk is whole milk or concentrated milk.

14. The method according to claim 8, wherein a starter culture is added to the milk before or simultaneously with the addition of the recombinant aspartic protease.

15. The method of claim 8, wherein said recombinant aspartic protease has 50% more, or greater, N-bound carbohydrates than found in the aspartic protease produced by the fungal source of the DNA molecule encoding said aspartic protease.

* * * * *